United States Patent [19]

Eriksen

[11] 4,180,586
[45] Dec. 25, 1979

[54] 3,4-DIPIVALYL-α-[METHYLAMINO)METHYL]BENZYL ALCOHOL AS AN ADJUNCT IN THE TREATMENT OF CIRCULATORY SHOCK

[75] Inventor: Stuart P. Eriksen, Santa Ana, Calif.

[73] Assignee: Interx Research Corporation, Lawrence, Kans.

[21] Appl. No.: 758,354

[22] Filed: Jan. 10, 1977

[51] Int. Cl.$^2$ ............................................. A61K 31/22
[52] U.S. Cl. .................................................... 424/311
[58] Field of Search ......................................... 424/311

[56] References Cited

U.S. PATENT DOCUMENTS 3,809,714  5/1974  Hussain et al. .................. 260/479 R

OTHER PUBLICATIONS

Bretschneider Monatsh., vol. 77 (1947), pp. 385–397.

*Primary Examiner*—Stanley J. Friedman
*Attorney, Agent, or Firm*—Burns, Doane, Swecker & Mathis

[57] ABSTRACT

A method for treating circulatory shock in warm-blooded animals via parenteral administration of 3,4-Dipivalyl-α-[(methylamino)methyl]benzyl alcohol and its nontoxic pharmaceutically acceptable acid addition salts is disclosed.

6 Claims, No Drawings

3,4-DIPIVALYL-α-[METHYLAMINO)METHYL]-BENZYL ALCOHOL AS AN ADJUNCT IN THE TREATMENT OF CIRCULATORY SHOCK

BACKGROUND OF THE INVENTION

1. Field of the Invention

The present invention is directed to a method for treating circulatory shock in warm-blooded animals, e.g., humans. More particularly, th present invention is concerned with a method for treating circulatory shock in warm-blooded animals by parenterally administering 3,4-Dipivalyl-α-[(methylamino)methyl]benzyl alcohol or any of its nontoxic pharmaceutically acceptable acid addition salts.

2. Description of the Prior Art

The attempted use of catecholamines and specifically 3,4,-Dihydroxyα-[(methylamino)methyl]benzyl alcohol (epinephrine) in the treatment of circulatory shock is essentially old in the art. However, the practical use of such agents is hardly desirable because of their overwhelming residual effect on the cardiovascular system. That is, administration of such agents, while generally alleviating circulatory shock, also produces, among other things, a cardiac excitatory action manifested by tachycardia, palpitation and an increase in the force of contraction of the heart muscle. Accordingly, it is readily apparent that the use of such agents in the treatment of circulatory shock is not a practical solution to the problem.

U.S. Pat. No. 3,809,714 discloses the subject compounds of the instant invention as adjuncts useful in the treatment of glaucoma and asthma, respectively. No mention or suggestion of the use of such compounds in the treatment of circulatory shock is noted.

It is obviously apparent that a need exists for a catecholamine derivative which not only is capable of alleviating circulatory shock in warm-blooded animals but is also free of the unwanted side effects previously noted.

SUMMARY OF THE INVENTION

Accordingly, it is an immediate object of this invention to provide a catecholamine adjunct and its nontoxic pharmaceutically acceptable acid addition salts for use in the treatment of circulatory shock in warm-blooded animals.

Another object of the invention is to provide a catecholamine adjunct which is essentially free from the unwanted cardiac side effects associated with the prior art.

Still another object of the invention is to provide a catecholamine adjunct which possesses increased stability and solubility such that it can be readily administered in standard, pharmaceutically acceptable parenteral formulations for parenteral administration.

Other objects, features and advantages of the invention will be made apparent to those of ordinary skill in the art from the detailed description of the invention which follows, taken in conjunction with the accompanying claims.

All the foregoing objects are achieved by parenterally administering to a warm-blooded animal suffering from circulatory shock, a sympathomimetic effective amount of 3,4-Dipivalyl-α-[(methylamino)methyl]benzyl alcohol or any nontoxic pharmaceutically acceptable acid addition salt thereof.

The phrase "nontoxic pharmaceutically acceptable acid addition salt" as used herein generally includes the nontoxic acid addition salts of the subject compound, formed with nontoxic inorganic or organic acids. For example, but without limitation, such salts would include those derived from inorganic acid such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, toluenesulfonic, methanesulfonic and the like.

Obviously, the term "3,4-Dipivalyl-α-[(methylamino)methyl]benzyl alcohol" denotes such compound in its racemic form as well as any of its resolved forms, that is, its d- or l- isomers.

Quite unexpectedly, it has been determined that the subject compound is unique in the treatment of circulatory shock in that it does not overwhelm the cardiovascular system as is the case with conventional catecholamines, i.e., epinephrine, but rather, the subject compound slowly but surely exerts a sympathomimetic activity which in turn elicits a sympathomimetic response sufficient to alleviate the circulatory shock in question without subsequent cardiac excitation. While the explanation for this is still speculative, it is believed that the uniqueness of the agent in question stems from its slow hydrolytic and/or enzymatic cleavage from 3,4-Dipivalyl-α-[(methylamino)methyl]benzyl alcohol to the parent moiety, epinephrine.

The subject compound and its nontoxic pharmaceutically acceptable acid addition salts are conveniently administered parenterally in the form of any nontoxic pharmaceutically acceptable parenteral solution. The parenteral vehicle can be any one of a number of conventional vehicles employed for parenteral administration, such as normal saline, parenteral polyethylene glycol, etc. As used herein, the term "parenterally" denotes administration via injection of the subject compound per se or in combination with a nontoxic pharmaceutically acceptable parenteral vehicle.

The dose administered, whether a single or multiple dose, will, of course, vary because of the needs and size of the recipient. The dose administered is not subject to definite bound;, however, it will usually be an effective sympathomimetic amount, or the equivalent on a molar basis of the pharmacologically active form produced upon the metabolic release of the active drug to achieve its desired or pharmacological and physiological effect. Normally, a dose range of from about 0.1 mg. to 100 mg should suffice.

From the foregoing description, one of ordinary skill in the art can easily ascertain the essential characteristics of this invention, and without departing from the spirit and scope thereof, can make various changes and modifications of the invention to adapt it to various usages and conditions. As such, these changes and modifications are properly, equitably and intended to be, within the full range of equivalence of the following claims.

What I claim is:

1. A method for treating circulatory shock in a warm-blooded animal suffering from same which comprises parenterally administering thereto, a sympathomimetic effective amount of the compound, 3,4-Dipivalyl-α-[(methylamino)methyl]benzyl alcohol or a nontoxic pharmaceutically acceptable acid addition salt thereof.

2. The method of claim 1, wherein said compound is administered in combination with a conventional non-toxic pharmaceutically acceptable parenteral vehicle.

3. The method of claim 2, wherein said parenteral vehicle is normal saline.

4. The method of claim 2, wherein said parenteral vehicle is parenteral polyethylene glycol.

5. The method of claim 1, wherein said compound is d-3,4-Dipivalyl-α-[(methylamino)methyl]benzyl alcohol.

6. The method of claim 1, wherein said compound is l-Dipivalyl-α-[(methylamino)methyl]benzyl alcohol.

* * * * *